United States Patent [19]

Koch et al.

[11] Patent Number: 4,832,029
[45] Date of Patent: May 23, 1989

[54] RADIATION ARRANGEMENT

[75] Inventors: Jochim Koch, Hollenbek; Wolfgang Franz, Lübeck, both of Fed. Rep. of Germany

[73] Assignee: Drägerwerk Aktiengesellschaft, Lübeck, Fed. Rep. of Germany

[21] Appl. No.: 68,904

[22] Filed: Jun. 30, 1987

[30] Foreign Application Priority Data

Jul. 2, 1986 [DE] Fed. Rep. of Germany ....... 3622148

[51] Int. Cl.⁴ .............................................. A61N 33/00
[52] U.S. Cl. ........................................ 128/376; 5/421; 362/130
[58] Field of Search ............... 128/395, 396, 376, 371, 128/399, 1 B; 5/421, 414, 505, 508; 362/127, 130, 131

[56] References Cited

U.S. PATENT DOCUMENTS

| 1,429,443 | 9/1922 | McFaddin | 128/395 |
| 1,669,468 | 5/1928 | Heintze | 128/396 |
| 2,744,186 | 5/1956 | Kamin | 362/130 |
| 3,085,568 | 4/1963 | Whitesell | 128/371 |
| 3,648,706 | 3/1972 | Holzer | 128/395 |
| 3,858,570 | 1/1975 | Beld et al. | 128/1 B |
| 3,877,437 | 4/1975 | Maitan et al. | 128/395 |
| 3,986,513 | 10/1976 | Stahl | 128/395 |
| 4,312,331 | 1/1982 | Hahmann | 128/1 B |
| 4,335,724 | 6/1982 | Frei et al. | 128/395 |

FOREIGN PATENT DOCUMENTS

| 1514331 | 4/1969 | Fed. Rep. of Germany | 128/395 |
| 2341433 | 2/1974 | Fed. Rep. of Germany | 128/1 B |
| 2776198 | 1/1976 | Fed. Rep. of Germany | . |
| 583043 | 7/1976 | Switzerland | 128/395 |

Primary Examiner—Richard C. Pinkham
Assistant Examiner—Mark S. Graham
Attorney, Agent, or Firm—Walter Ottesen

[57] ABSTRACT

A radiation arrangement provides heat to a bed surface for accommodating a patient thereon. Heat sources are arranged at a spatial distance above the bed surface in such a way that uniform radiant warming of the bed surface is obtained and that sides of the bed surface are maintained clear of radiation to facilitate access by persons attending the patient so that these attending persons are not subjected to the radiant heat especially in the region of the head. The arrangement includes small-surface heat radiators which are located and spaced vertically above the corner points of a polygon border enclosing the bed surface.

6 Claims, 1 Drawing Sheet

RADIATION ARRANGEMENT

FIELD OF THE INVENTION

The invention relates to a radiation arrangement for supplying heat to a bed surface for accommodating a person. The radiation arrangement includes a heat source mounted above the bed surface so as to be spaced therefrom.

BACKGROUND OF THE INVENTION

Radiation arrangements of this kind are used for keeping warm, premature babies, infants, and small children, who lie on a bed surface accessible from several sides and thus can be attended to by the appropriate personnel without hindrance.

Because of the necessary ability to examine the patient, and in order to have the highest possible freedom of movement during the treatment procedure of the patient, these radiation heaters are provided only in a portion of the region above the bed surface.

Thus, for example, in U.S. Pat. No. 4,312,331, a treatment table for newborn babies and small children is described, above the center region of which an elongated narrow radiation heater is arranged. One such known radiation heater warms intensively the central portion of the bed surface while, because of the heat energy radially decreasing towards the border region of the bed surface, there is too little radiation energy present to supply the patient with sufficient heat energy. However, a uniform warming of the entire bed surface with heat energy evenly distributed thereover is necessary because the person to be attended to, as a consequence of his or her size, covers different areas of the bed surface and because that person must be moved during treatment to different areas on the bed surface.

A further radiation heater is disclosed in German Utility Model Registration No. 76 02 145 and is installed above the bed surface in such a way that the heat radiator is of planar configuration and nearly corresponds in its diemsnions with the dimensions of the bed surface. However, this solution presents the disadvantage that the attending personnel, who must have access from the free sides to the person lying on the bed surface and must bend above the bed surface in the course of the treatment activity, are exposed to the radiation heat at the region of the head. This leads in the case of a prolonged and continuing treatment to an intolerable heat exposure of the attending personnel and shades the patient.

SUMMARY OF THE INVENTION

It is an object of the invention to provide a radiation arrangement wherein the bed surface is uniformly warmed by the radiation and wherein the access sides for attending personnel are maintained clear of the radiation directed to the bed surface.

According to a feature of the radiation arrangement of the invention, small-surface heat radiators are provided which are placed at a vertical spatial distance above the corner points of a polygon border surrounding the bed region.

The advantage of the invention is essentially seen in that, independently of the larger geometric form of the bed surface, the heat radiators are arranged above the corner points of a polygon so that each of the heat radiators irradiates the bed surface from its location with a cone of radiation which leaves adequate space free of radiation for the personnel attending the patient.

A further advantage of the invention is that radiation heat applied to the person on the bed surface from the corner locations can be directed better onto the side surfaces of the person to be warmed in a greater proportion than is the case with the known radiation apparatus. For this purpose, it is only necessary to adjust correspondingly the distance of the heat radiator from the bed region. Depending upon where on the bed surface that the patient is located, individual heat radiators can be purposely directed at the patient by means of small pivoting movements of these heat radiators.

To further augment the heat radiation, an additional heat radiator can be advantageously provided in the center region of and above the polygon.

Suitably, the area above the center region of the polygon can be provided to receive an additional radiation lamp whose radiation intensity lies in a different wavelength region than that of the remaining warming radiators. This can be, for example, a blue-light radiator suitable for performing phototherapy on premature and newborn babies. With this arrangement, it is possible to apply warming radiation in combination with phototherapy with the advantage of large-area radiation warming of the patient. Preferably, the blue-light radiation has a maximum radiation intensity in the wavelength range of 400 to 550 nm.

Advantageously, the heat radiators can be combined with light radiators for the white light. In this way, a true and natural illumination of the bed surface and observation of the patient is possible.

It has been found particularly appropriate to use as heat radiators ceramic high-temperature radiators which exhibit a small, highly tempered radiation surface, which can be aligned in different ways with respect to their direction of radiation according to need.

BRIEF DESCRIPTION OF THE DRAWINGS

The invention will now be described with reference to the drawing wherein.

DESCRIPTION OF THE PREFERRED EMBODIMENTS OF THE INVENTION

Figure 1:
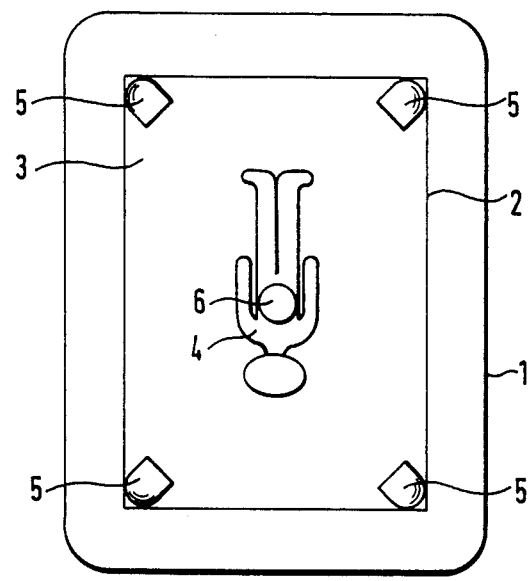
FIG. 1 is a top plan view of a bed surface and radiation arrangement according to the invention; and, FIG. 2 is an elevation end view of the bed surface with the heat radiators.

The top plan view of FIG. 1 includes the schematic outline of a patient 4 lying at the center of the bed surface 1. The region 3 in which the patient 4 lies is bounded by a polygon which is shown here in the form of a rectangle. Heat radiators 5 are mounted in the corners of the rectangle 2 and are positioned so that the radiation thereof is directed onto the body of the patient 4. A further radiator 6 is arranged above the center region of the rectangle 2 as a heat radiator for directly radiating the center region of the bed surface 1.

Figure 2:
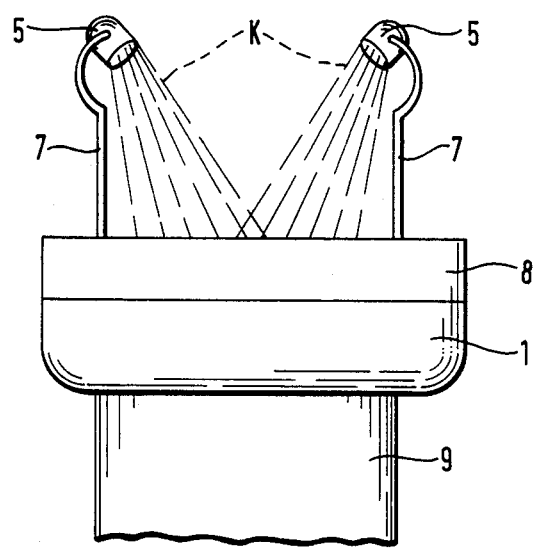

FIG. 2 represents a partial view of the bed surface 1 viewed in the direction toward one of its longitudinal ends. The bed surface 1 is surrounded by a border 8 and rests on a base 9. The heat radiators 5 are held above the bed surface 1 on respective posts 7 and can be adjusted with respect to the direction (K) of their radiation so that the latter falls onto the bed region 3.

By arranging the heat radiators 5 in the corners of the rectangle 2, the sides of the rectangular bed surface 3 remain free of radiant heat so that a radiation-free zone is formed at the elevation of the heat radiators 5. The personnel attending the patient 4 may enter through this radiation free zone without being subjected to annoying heat radiation in the region of the head.

It is understood that the foregoing description is that of the preferred embodiments of the invention and that various changes and modifications may be made thereto without departing from the spirit and scope of the invention as defined in the appended claims.

What is claimed is:

1. A radiation arrangement for supplying heat to a person, the radiation arrangement comprising:
   a bed surface for accommodating the person thereon;
   a polygonal border surrounding said bed surface and defining a plurality of corners;
   a plurality of heat radiators;
   support means for mounting said heat radiators so as to be vertically positioned exclusively and only above corresponding ones of said corners; and,
   said heat radiators being point-source directional heat radiators configured to issue and direct their radiation toward said bed surface in the form of a plurality of radiation cones to irradiate said bed surface and so as to leave a radiation-free zone between each two mutually adjacent ones of said cones which extends downwardly toward said bed surface in which attending personnel can attend the person on said bed surface from a position between any two mutually adjacent ones of said heat radiators without the head region of the attending personnel being exposed to the heat radiation in said radiating cones.

2. The radiation arrangement of claim 1, comprising a blue-light radiator arranged above the central region enclosed by said polygonal border and having a maximum radiation intensity lying in the wavelength range of 400 to 550 nm.

3. A radiation arrangement for supplying heat to a person, the radiation arrangement comprising:
   a bed surface for accommodating the person thereon;
   a polygonal border surrounding said bed surface and defining a plurality of corners;
   a plurality of heat radiators;
   first support means for mounting said heat radiators so as to be vertically positioned exclusively and only above corresponding ones of a first group of said corners;
   a plurality of light radiators;
   second support means for mounting said light radiators so as to be vertically spaced above corresponding ones of a second group of said corners; and,
   said heat radiators being point-source directional heat radiators configured to issue and direct their radiation toward said bed surface in the form of a plurality of radiating cones to irradiate said bed surface and so as to leave a radiation-free zone between each two mutually adjacent ones of said cones which extends downwardly toward said bed surface in which attending personnel can attend the person on said bed surface from a position between any two mutually adjacent ones of said heat radiators without the head region of the attending personnel being exposed to the heat radiation in said radiating cones.

4. The radiation arrangement of claim 3, comprising at least one additional light radiator arranged above the central region enclosed by said polygonal border.

5. A radiation arrangement for supplying heat to a person, the radiation arrangement comprising:
   a bed surface for accommodating the person thereon;
   a polygonal border surrounding said bed surface and defining a plurality of corners;
   a plurality of heat radiators;
   support means for mounting said heat radiators so as to be vertically positioned exclusively and only above corresponding ones of selected ones of said corners; and,
   said heat radiators being point-source directional heat radiators configured to issue and direct their radiation toward said bed surface in the form of a plurality of radiating cones to irradiate said bed surface and so as to leave a radiation-free zone between each two mutually adjacent ones of said cones which extends downwardly toward said bed surface in which attending personnel can attend the person on said bed surface from a position between any two mutually adjacent ones of said heat radiators without the head region of the attending personnel being exposed to the heat radiation in said radiating cones.

6. The radiation arrangement of claim 5, said polygonal border being a rectangular border defining four corners; said plurality of small-surface heat radiators being four in number; and, said support means being four posts mounted at corresponding ones of said four corners for holding respective ones of said heat radiators.

* * * * *